United States Patent [19]

Kötzsch et al.

[11] Patent Number: 4,647,681
[45] Date of Patent: Mar. 3, 1987

[54] METHOD FOR THE PREPARATION OF PERSILYLATED CARBOXYLIC ACID AMIDES

[75] Inventors: Hans-Joachim Kötzsch, Rheinfelden; Hans-Joachim Vahlensieck, Wehr, both of Fed. Rep. of Germany

[73] Assignee: Dynamit Nobel AG, Cologne, Fed. Rep. of Germany

[21] Appl. No.: 800,996

[22] Filed: Nov. 22, 1985

[30] Foreign Application Priority Data

Dec. 1, 1984 [DE] Fed. Rep. of Germany ....... 3443960

[51] Int. Cl.$^4$ ................................................ C07F 7/10
[52] U.S. Cl. .................................................... 556/411
[58] Field of Search .......................................... 556/411

[56] References Cited

U.S. PATENT DOCUMENTS

| 3,415,864 | 12/1968 | Gehrke et al. | 556/411 |
| 3,488,371 | 1/1970 | Klebe | 556/411 |
| 3,839,387 | 10/1974 | Chou et al. | 556/411 |
| 4,059,559 | 11/1977 | Burkhardt et al. | 556/411 |

*Primary Examiner*—Paul F. Shaver
*Attorney, Agent, or Firm*—Felfe & Lynch

[57] ABSTRACT

Disclosed is a method of preparing bis-trimethylsilylamides of carboxylic acids from the carboxylic acid amide by mixing two equivalents of trimethylchlorosilane and an excess of hexamethyldisilazane, heating the mixture to 40° to 80° C. and adding two equivalents of a tertiary amine as acid acceptor. The method results in substantially improved purity and yield of end product.

6 Claims, No Drawings

METHOD FOR THE PREPARATION OF PERSILYLATED CARBOXYLIC ACID AMIDES

BACKGROUND OF THE INVENTION

The invention relates to a method for the persilylation of carboxylic acid amides of the general formula R—CONH$_2$ (I) by means of trimethylchlorosilane and tertiary amines, to form the N.N-bis- and/or N.O-bis-trimethylsilylcarboxylic acid amides of the formulas

 (II)

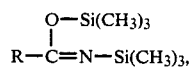 (III)

the N.O isomers of formula III being preferred. II was not separated from III.

In these formulas R preferably represents H, CH$_3$, C$_2$H$_5$, C$_3$H$_7$, CH(CH$_3$)$_2$, CH$_2$=CH, CH$_2$=C(CH$_3$), CH$_2$F, CHF$_2$ or CF$_3$.

Compounds of formula II (R=CH$_3$) are formed, according to Chem. Abstr. 57, 11224a, from hexamethyldisilazane by acetylation with ketene, but only in addition to large percentages of the byproducts acetonitrile and hexamethyldisiloxane which are not desirable in this case.

Also the acetylation of hexamethyldisilazane with acetyl chloride gives only moderate yields of products II and III, because the product that has formed reacts with acid chloride, the same as the starting silane, and forms a series of by-products.

The conventional preparation of the substances of formulas II and/or III from amides with trimethylchlorosilane in the presence of tertiary amines as acid acceptors leads to the formation of two equivalents of the tertiary amine hydrochloride in solid form for each amide function of the acid amide. On account of the great amount of solid produced, preparation in the presence of solvents has been attempted (Chem. Abstr. 65, 7025d), but this impairs the completeness of the reaction and hence the yield. The use of trimethylchlorosilane in excess (Chem. Abs. 59, 1673 b) makes the working up of the product difficult and leads to very high chloride contents in the end product. In addition, the danger of delayed reaction exists in this case. Generally, a rather unstable product forms, which tends to degrade to nitriles and hexamethyldisiloxane. This property of the product is especially undesirable on account of poor storage life. Moreover, the yield is still in need of improvement. It has therefore been proposed that amides be reacted with hexamethyldisilazane (G. Schirawski, U. Wannagat, Monatshefte Chem. 1969, 100 (6), 1901-9). In that case, however, monosilylation products form and not products II and III. By-products having a triazine structure are a special disadvantage in this case. Moreover, undesired, unusable ammonia is released when such a procedure is employed.

Accordingly, the problem existed of finding an improved method of preparation without the above-described disadvantages, which above all would deliver a more stable product of good shelf life and improve the yield.

THE INVENTION

The subject matter of the invention is a method for the preparation of bis-trimethylsilylamides from carboxylic acid amides by silylation with trimethylchlorosilane and tertiary amines, characterized by combining acid amide with two equivalents of trimethylchlorosilane for each amide function, adding hexamethyldisilazane, dosing into the mixture two equivalents of a tertiary amine at 40° to 80° C., separating, after the reaction, the solid consisting mainly of the hydrochloride of the tertiary amine, and working up the liquid reaction products by distillation.

The solution of this problem was obtained according to the invention by placing the acid amide in question in a reactor together with two moles of trimethylchlorosilane for each amide function of the acid amide in the presence of hexamethyldisilazane—a mixture which at first does not react—, heating the mixture to at least 40° C., and gradually adding two moles of tertiary amine, without exceeding a maximum temperature of 80° C. It is possible to depart by as much as 10%, for example, from the above-mentioned molar and equivalent ratios, but the disadvantage of unreacted parts will result. The presence of hexamethyldisilogene is necessary, according to the invention, in catalytic concentrations of 0.1 to 2.0 mol-% with respect to the carboxylic acid amide. Hexamethyldisilazane can also be used according to the invention in a larger amount, generally in amounts of up to 8 equivalents, e.g., as diluents, and this is preferred.

The working up of the product is performed in a manner known in itself by the common methods of separation of solids and vacuum distillation, and of the recycling of the tertiary amine according to the invention is accomplished by displacing the amine from the tertiary amine hydrochloride by means of ammonia with the formation of ammonium chloride. Water is to be excluded from the reaction.

We have found that hexamethyldisilazane surprisingly does go into reaction, but is reconstituted almost completely.

The overall reaction therefore takes place according to the equation:

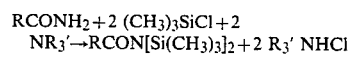

The tertiary amine R$_3'$ N can be recovered from the separated hydrochloride by distillation with the aid of preferably anhydrous ammonia at temperatures up to 80° C. The only by-product of the process is NH$_4$Cl in pure form.

The method achieves a virtually quantitative yield of products II and III. The product has superior purity. The product no longer tends to decompose with the formation of nitrile and hexamethyldisiloxane and therefore for the first time enjoys an unlimited shelf life.

Examples of carboxylic acid amides of the general formula RCONH$_2$ (I) suitable for the method of the invention are formamide, acetamide, propionic acid amide, isobutyramide, acrylamide, methacrylamide, fluoroacetic acid amide, difluoroacetic acid amide and trifluoroacetic acid amide. Diamides of the dicarboxylic acids, such as oxalic acid diamide, are also suitable.

Tertiary amines which can be used as acid receptors are, for example, trimethylamine, triethylamine, tributylamine, pyridine etc. According to the invention they are fed gradually into the mixture contained in the reactor while maintaining a temperature between 40° and 80° C.

Examples of the products of formulas II and III which can be prepared are:
bis-trimethylsilylformamide,
bis-trimethylsilylacetamide,
bis-trimethylsilylpropionamide,
bis-trimethylsilylacrylamide,
bis-trimethylsilylmethacrylamide,
bis-trimethylsilyltrifluoracetamide, etc.

A suitable apparatus for the performance of the process according to the invention is a stirrer reactor with reflux condenser and dosing apparatus, which is equipped in the usual manner for operation with the exclusion of moisture and for keeping the reactor temperature at 40° to 80° C.

The raw product solution is filtered from the reacted mixture through a filter apparatus, for example filtered from the tertiary amine hydrochloride in a centrifuge, and is transferred to the body of a vacuum distillation column, and fractionally distilled. The filter cake is washed with hexamethyldisilazane and transferred to a solid-matter stirring apparatus, such as an anchor stirring vessel or paddle dryer equipped with a vacuum distillation system, and it is dried by low vacuum distillation and saturated with ammonia. This releases the tertiary amine again. It is distilled out and reused. At the same time the ammonium chloride, which substantially does not sublime at 40° to 80° C., is dried.

The persilylated carboxylic acid amides of formulas II and III prepared by the method of the invention serve especially as silylating agents and protective-group reagents, for example in the synthesis of antibiotics and for the treatment of solid-bed catalysts.

EXAMPLES

Example 1

Preparation of bis-trimethylsilylformamide

In a 250-liter stirrer reactor having a thermostat-controlled heating and cooling circuit in its jacket, a reflux condenser (nitrogen as the protective gas) and a submerged gas introduction tube, 9 kg of anhydrous formamide (0.2 kmol) and 21.7 kg of trimethylchlorosilane (0.4 kmol) were mixed and heated in 140 liters of hexamethyldisilazane. Beginning when the reactor temperature reached 48° C., 23.6 kg (0.4 kmol) of trimethylamine was introduced through a flow meter at a rate of about 0.2 kmol/h over a period of about two hours, whereupon a reactor temperature of about 54° C. established itself and trimethylamine hydrochloride crystalized out. After the addition of the amine had ended, stirring was continued for four hours at about 56° C. to complete the reaction, and then the mixture was cooled down to room temperature.

To work up the mixture, the fully reacted suspension of the product was taken from the reactor by a paring centrifuge and the solid trimethylammonium chloride (approx. 40 kg) was separated and washed twice, each time with 10 liters of hexamethyldisilazane.

The centrifugally separated trimethylammonium chloride was transferred to a paddle dryer, a vacuum was applied, and the vacuum was relieved with about 8 kg of gaseous ammonia. The temperature was raised to about 80° C. under the pressure that naturally developed, and finally the pressure was let off by carefully opening the vapor line, while the released trimethylamine distilled in a deep-freeze receiver (yield about 20 kg) for reuse. After changing the receiver, the dryer was evacuated to about 25 mbar while maintaining a dryer temperature of 80° C., and approximately another 4 kg of hexamethyldisilazane distilled off. Then 21 kg of ammonium chloride was emptied from the dryer in the form of a white powder.

The filtrate with the product it contained was transferred to the body of a column-type vacuum still, heated to 80° C. by a heating fluid, and fractionated in vacuo. After the hexamethyldisilazane has been recovered as the first fraction, a total of 35.2 kg of bis-trimethylsilylformamide was isolated in pure form by distillation: b.p. 39° C. (6 mbar). Yield 92.9%.

Example 2

Preparation of bis-trimethylsilylacetamide

In a two cubic meter stirrer reactor with a heating and cooling circuit in its jacket, a reflux condenser (nitrogen protective gas) and gas introduction tube, 120 kg (2 kmol) of water- and acid-free acetamide together with 434 kg (4 kmol) of trimethylchlorosilane was suspended in 1.2 cubic meters of hexamethyldisilazane and heated. Beginning when the internal temperature of the reactor reached 52° C., a total of 238 kg (approx. 4 kmol) of trimethylamine was introduced through a flow meter at a rate of about 2.4 kmol/h for a period of approximately 100 minutes, while the reactor temperature was raised by means of the heating circuit to about 74° C. After the amine had been added, the mixture was stirred for six hours at about 74° C. to complete the reaction.

To work up the mixture, the fully reacted suspension of the raw product from the reactor was separated by an automatically operating siphoning centrifuge into the solid trimethylammonium chloride (approx. 420 kg) and the raw product filtrate.

A work-up similar to Example 1 yielded--in addition to the recovery of about 230 kg of trimethylamine and the hexamethylenedisilazane plus the 212 kg of usable ammonium chloride that was produced—390 kg of bis-trimethylsilylacetamide, b.p. 42° C. (9 mbar), mostly in the N.O form as imido ester, mixed with a low concentration of the N.N form. Yield 95.8%.

Example 3

Preparation of bis-trimethylsilyltrifluoroacetamide

In an apparatus similar to that of Example 1, with a liquid dosing apparatus instead of the gas introduction tube, 18.1 kg (0.16 kmol) of trifluoroacetamide and 34.75 kg (0.32 kmol) of trimethylchlorosilane were reacted similarly to Example 1 in 130 liters of hexamethyldisilazane by the dosed input of 25.3 kg (0.32 kmol) of pyridine and continuing to stir at 70° C.

By similar work-up, after the separation of about 40 kg of pyridine hydrochloride, and after recovering about 25 kg of pyridine, approximately 17 kg of ammonium chloride and the input hexamethyldisilazane, 37.2 kg of bis-trimethylsilyltrifluoroacetamide, b.p. 40° C. (25 mbar) was isolated through a 30-tray column. Yield 91%.

Example 4

Preparation of bis-trimethylsilylpropionic acid amide

In a manner similar to Example 1, using a liquid dosing apparatus instead of the gas introduction tube on the reactor, 11 kg (0.15 kmol) of propionamide and 32.6 kg (0.3 kmol) of trimethylchlorosilane were reacted by the dosed input of 30.5 kg (0.3 kmol) of triethylamine, beginning at 55° C. and after-stirring at 75° C.

The similar work-up and separation of about 45 kg of triethylammonium chloride yielded, in addition to the recovered hexamethyldisilazane, ammonium chloride (about 16 kg) and triethylamine (about 30 kg), the bis-trimethylsilylpropionic acid amide, b.p. 42° C. (3 mbar), in a yield totaling 29.8 kg (91.6%).

Example 5

Preparation of bis-trimethylsilylacrylamide

In a ten-liter stirrer reactor with a thermostat-controlled heating and cooling circuit in its jacket, and with a nitrogen-shielded reflux condenser, internal thermometer and submerged gas introduction tube, 2.884 g (4 mol) of acrylic acid amide (stabilized with 200 mg of copper powder) and 870 g (8 mol) of trimethylchlorosilane were stirred in 5 liters of hexamethyldisilazane, heated at 45° C., and brought to reaction by the introduction of 480 g (approximately 8 mol) of trimethylamine over a period of two hours. After completion of the reaction by six hours of after-stirring at 64° C., the trimethylammonium chloride (approx. 800 g) was separated by centrifugation with the exclusion of air and moisture.

Upon vacuum distillation through a Sulzer column with monel metal packing, while feeding into it pure oxygen in traces for stabilization, the filtrate yielded 764 g (89%) of bis-trimethylsilylacrylamide, b.p. 38° to 39° C. (2 mbar).

It will be understood that the specification and examples are illustrative but not limitative of the present invention and that other embodiments within the spirit and scope of the invention will suggest themselves to those skilled in the art.

We claim:

1. A method of preparing bis-trimethylsilyl amides comprising adding acid amide in a reactor with two equivalents of trimethylchlorosilane for each amide function with the addition of hexamethyldisilazane to form a mixture, reacting the mixture by heating it to 40° to 80° C. while dosing the mixture with two equivalents of a tertiary amine; separating from the reacted mixture solids, consisting mainly of the hydrochloride of the tertiary amine, and working up liquid reaction products by distillation.

2. The method of claim 1, wherein the acid amide is of the formula $R-CONH_2$ where R is H, $CH_3 C_2H_5, C_3H_7$, $CH(CH_3)_2$, $CH_2=CH$, $CH_2=C(CH_3)$, $CH_2F$, $CHF_2$ or $CF_3$.

3. The method of claim 1, wherein the tertiary amine is trimethylamine, triethylamine, tributylamine, or pyridine.

4. The method of claim 1, wherein the tertiary amine is released with ammonia from the separated hydrochloride of the tertiary amine.

5. The method of claim 1, wherein the acid amide is a diamide of a dicarboxylic acid.

6. The method of claim 5, wherein the acid amide is oxalic acid diamide.

* * * * *